(12) United States Patent
Shareef et al.

(10) Patent No.: US 8,366,653 B2
(45) Date of Patent: Feb. 5, 2013

(54) INTRAOCULAR PRESSURE REGULATING DEVICE

(75) Inventors: Shakeel R. Shareef, Pittsford, NY (US); Mustafa A. G. Abushagur, Rochester, NY (US)

(73) Assignee: University of Rochester, Rochester, NY (US)

( * ) Notice: Subject to any disclaimer, the term of this patent is extended or adjusted under 35 U.S.C. 154(b) by 314 days.

(21) Appl. No.: 12/531,293

(22) PCT Filed: Mar. 13, 2008

(86) PCT No.: PCT/US2008/056913
§ 371 (c)(1), (2), (4) Date: Aug. 24, 2010

(87) PCT Pub. No.: WO2008/112935
PCT Pub. Date: Sep. 18, 2008

(65) Prior Publication Data
US 2011/0046728 A1    Feb. 24, 2011

Related U.S. Application Data

(60) Provisional application No. 60/906,960, filed on Mar. 13, 2007.

(51) Int. Cl.
*A61F 2/14* (2006.01)
*A61F 2/16* (2006.01)
(52) U.S. Cl. .......................... 604/9; 623/6.39; 623/6.42
(58) Field of Classification Search ............... 604/9; 623/6.39–6.42, 6.51
See application file for complete search history.

(56) References Cited

U.S. PATENT DOCUMENTS

| | | |
|---|---|---|
| 5,283,063 A | 2/1994 | Freeman |
| 6,450,984 B1 | 9/2002 | Lynch et al. |
| 6,494,857 B1 | 12/2002 | Neuhann |
| 7,090,888 B2 * | 8/2006 | Snyder et al. ............ 427/2.21 |
| 7,708,711 B2 * | 5/2010 | Tu et al. ................... 604/8 |
| 2003/0208163 A1 * | 11/2003 | Yaron et al. .............. 604/187 |
| 2004/0098126 A1 | 5/2004 | Freeman et al. |
| 2004/0193262 A1 * | 9/2004 | Shadduck ................. 623/4.1 |

* cited by examiner

*Primary Examiner* — Tatyana Zalukaeva
*Assistant Examiner* — Benjamin Klein
(74) *Attorney, Agent, or Firm* — James W. Hill; McDermott Will & Emery LLP

(57) ABSTRACT

Systems and methods are described for implanting a device in a mammalian eye to raise intraocular pressure. In some embodiments, the device (54) includes an arcuate body that, when implanted, obstructs aqueous humor outflow from the anterior chamber (38) of the eye.

10 Claims, 10 Drawing Sheets

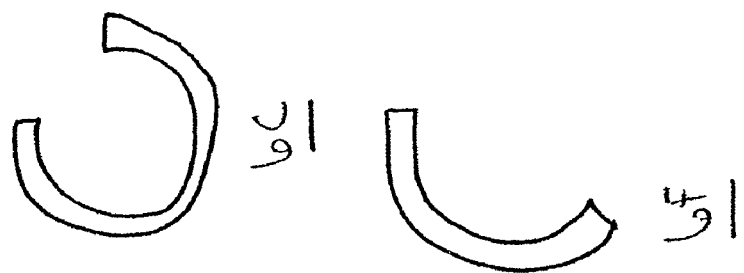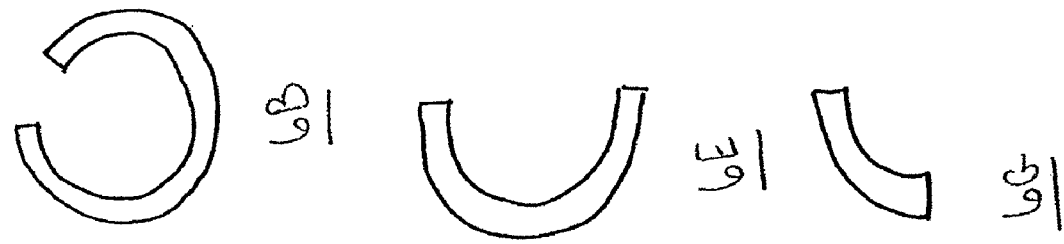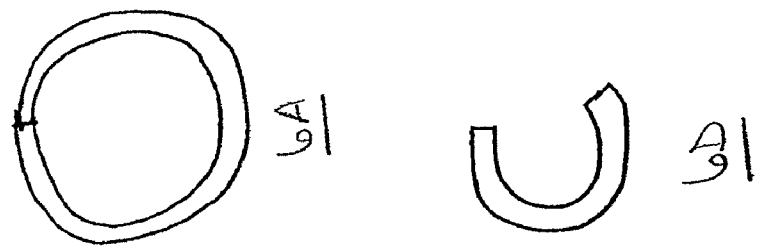
FIG. 6

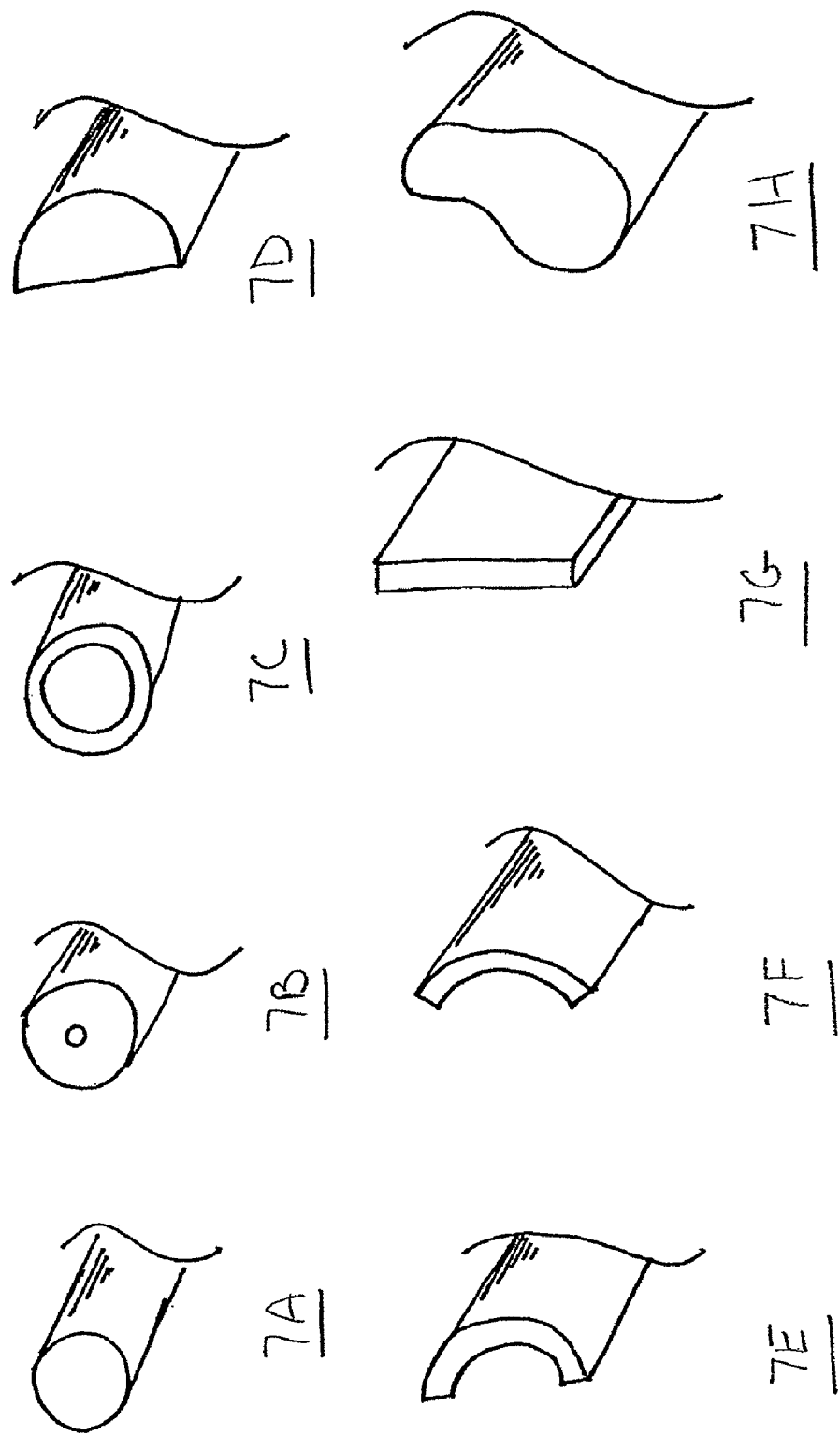

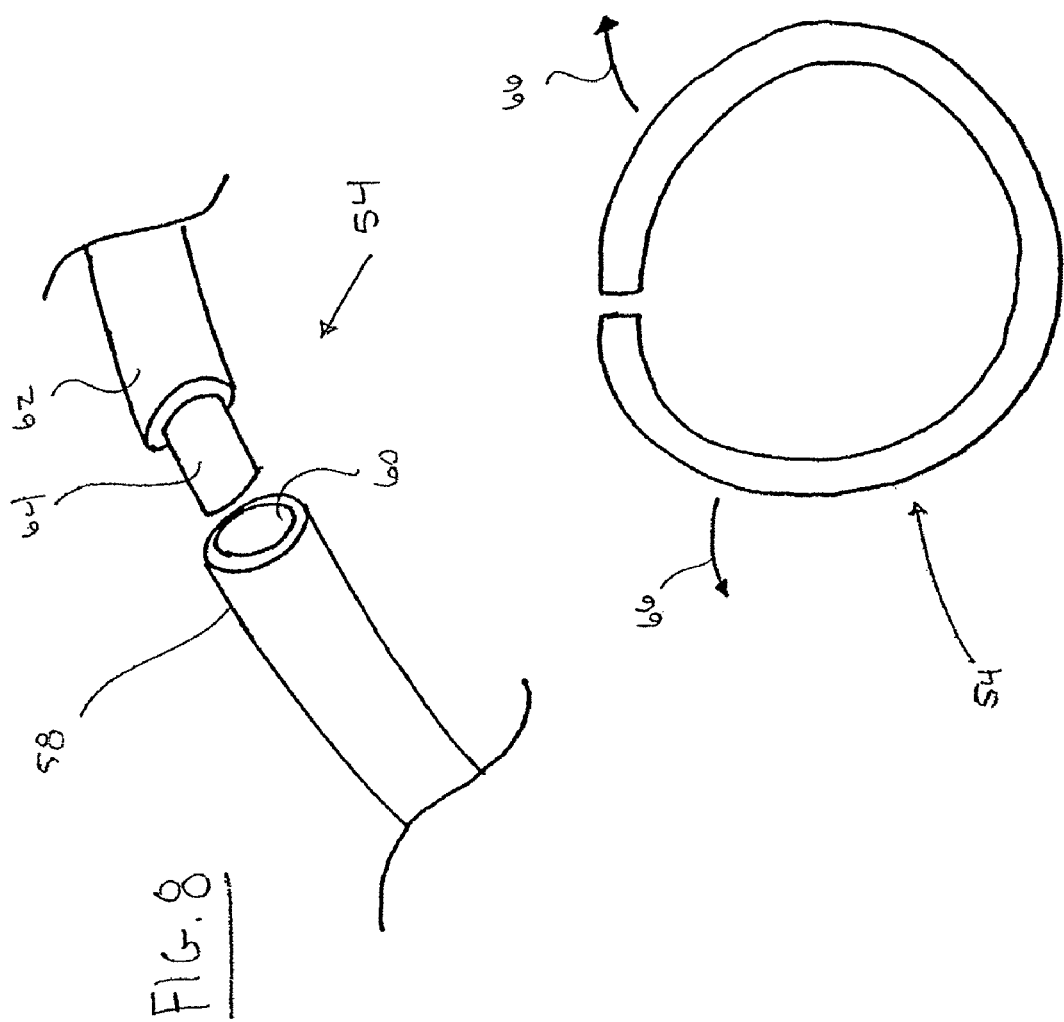

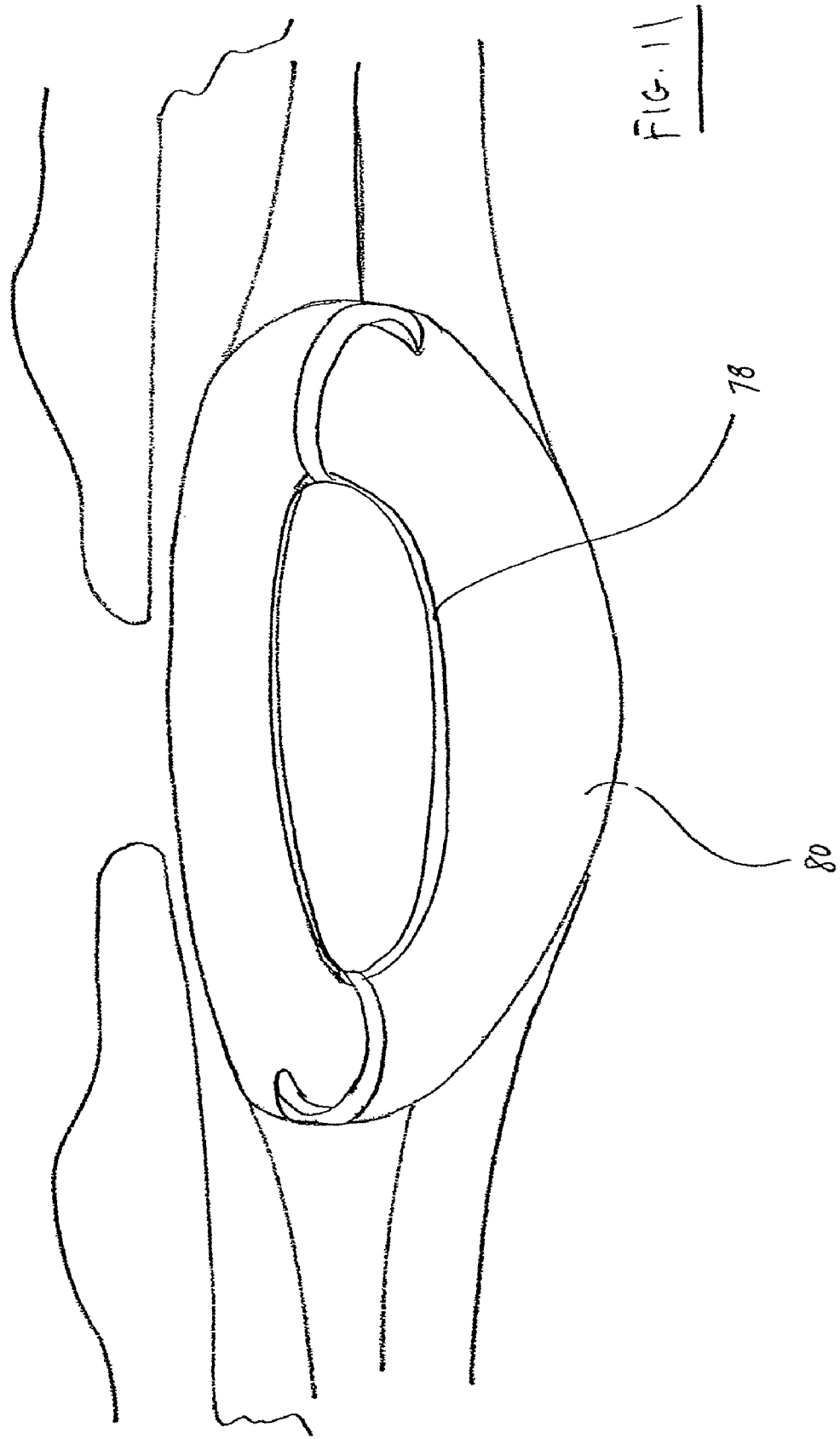

INTRAOCULAR PRESSURE REGULATING DEVICE

RELATED APPLICATIONS

This application claims the priority benefit of U.S. Provisional Application No. 60/906,960, filed Mar. 13, 2007, the entirety of which is incorporated herein by reference.

FIELD

This disclosure relates to systems and methods for treatment of glaucoma, and, more specifically to, systems and methods for creating a model that simulates glaucoma and for treatment of hypotonous eyes.

BACKGROUND

About two percent of people in the United States have glaucoma. Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated.

Glaucoma is grossly classified into two categories: closed-angle glaucoma, also known as "angle closure" glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous humor from the anterior chamber of the eye.

Open-angle glaucoma is any glaucoma in which the angle of the anterior chamber remains open, but the exit of aqueous through the trabecular meshwork or other natural outflow pathways is diminished. Primary open-angle glaucoma is the most common of the glaucomas, and it is often asymptomatic in the early to moderately advanced stage. Patients may suffer substantial, irreversible vision loss prior to diagnosis and treatment. However, there are secondary open-angle glaucomas which may include edema or swelling of the trabecular spaces (e.g., from corticosteroid use), abnormal pigment dispersion, or diseases such as hyperthyroidism that produce vascular congestion.

Current therapies for glaucoma are directed at decreasing intraocular pressure. Medical therapy includes topical ophthalmic drops or oral medications that reduce the production or increase the outflow of aqueous. These drug therapies for glaucoma are sometimes associated with significant side effects, such as headache, blurred vision, allergic reactions, death from cardiopulmonary complications, and potential interactions with other drugs. When drug therapy fails, surgical therapy is used. Surgical therapy for open-angle glaucoma consists of laser trabeculoplasty, trabeculectomy, and implantation of aqueous shunts after failure of trabeculectomy or if trabeculectomy is unlikely to succeed. Trabeculectomy is a major surgery that is widely used and is augmented with topically applied anticancer drugs, such as 5-flurouracil or mitomycin-C, to decrease scarring and increase the likelihood of surgical success.

SUMMARY

Described herein are in embodiments directed to systems and methods for creating a model that simulates an eye with glaucoma. Specifically, the systems and methods include in embodiments for increasing the intraocular pressure of an eye by limiting the outflow of aqueous from the eye. Further in embodiments are direct it to systems and methods for treating a hypotonous eye by limiting the outflow of aqueous from the eye.

In some embodiments, systems and methods are described for implanting a device in a mammalian eye to raise intraocular pressure. Some embodiments include an arcuate body that, when implanted, obstructs aqueous humor outflow from the anterior chamber of the eye. In some embodiments, the arcuate body acts as a spring, exerting a bias force tending to increase a radius of curvature of the body when implanted in eye. In some embodiments, the arcuate body is a capsular tension arc. Some embodiments provide that the arcuate body has an outer curved surface conforming to a curved inner surface of the eye. In certain embodiments, the arcuate body, when implanted, contacts the trabecular meshwork of the eye. In some embodiments, the arcuate body, when implanted, contacts the iris of the eye. Some embodiments provide that the arcuate body, when implanted, resides in the lens capsular bag of the eye. In some embodiments, the arcuate body, when implanted, produces ischemia in aqueous outflow pathway tissues.

In certain embodiments, the outflow pathway tissues comprise the trabecular meshwork. Various embodiments provide that the arcuate body extends in at least 20°, 40°, 60°, 90°, 120°, 180°, 270°, and 360°. In some embodiments, the device, when implanted, effectively treats hypotony of the eye. In certain embodiments, the arcuate body comprises at least one aperture that permits passage of aqueous therethrough. In some embodiments, the arcuate body is porous.

Some methods described herein, of elevating intraocular pressure in a mammalian eye, include inserting a device in the eye and raising intraocular pressure with the device. In some methods, the raising the intraocular pressure comprises at least partially obstructing outflow of aqueous humor from the anterior chamber of the eye. Certain methods further include adjusting an amount of obstruction of the outflow. Certain methods further include selecting a size of the device, prior to the inserting, using ocular imaging. Certain methods further include modeling glaucoma using the device after the inserting of the device in the eye. Certain methods further include treating hypotony of the eye using the device by the inserting of the device in the eye.

In some methods, the inserting comprises inserting the device into the anterior chamber of the eye. Some methods provide that the device is inserted into the iridocorneal angle. In some methods, the inserting comprises inserting the device into the posterior chamber of the eye. Certain methods provide that the device is inserted into the lens capsular bag. Some methods further include permitting passage of aqueous humor through at least one aperture in the device. Certain methods further include permitting passage of aqueous humor through pores in the device.

For purposes of summarizing the disclosure, certain aspects, advantages, and novel features of the disclosure have been described herein. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages as may be taught or suggested herein.

BRIEF DESCRIPTION OF THE DRAWINGS

A general architecture that implements various features of the disclosure will now be described with reference to the drawings. The drawings and the associated descriptions are provided to illustrate embodiments of the disclosure and not to limit the scope of the disclosure. Throughout the drawings, reference numbers are re-used to indicate correspondence between referenced elements.

FIG. 6A depicts a schematic top view of embodiments of a device for implantation within the eye.

FIG. 6B depicts a schematic top view of embodiments of a device for implantation within the eye.

FIG. 6C depicts a schematic top view of embodiments of a device for implantation within the eye.

FIG. 6D depicts a schematic top view of embodiments of a device for implantation within the eye.

FIG. 6E depicts a schematic top view of embodiments of a device for implantation within the eye.

FIG. 6F depicts a schematic top view of embodiments of a device for implantation within the eye.

FIG. 6G depicts a schematic top view of embodiments of a device for implantation within the eye.

FIG. 7A depicts a perspective views of embodiments of a device for implantation within the eye, showing a cross-section profile of the device.

FIG. 7B depicts a perspective views of embodiments of a device for implantation within the eye, showing a cross-section profile of the device.

FIG. 7C depicts a perspective views of embodiments of a device for implantation within the eye, showing a cross-section profile of the device.

FIG. 7D depicts a perspective views of embodiments of a device for implantation within the eye, showing a cross-section profile of the device.

FIG. 7E depicts a perspective views of embodiments of a device for implantation within the eye, showing a cross-section profile of the device.

FIG. 7F depicts a perspective views of embodiments of a device for implantation within the eye, showing a cross-section profile of the device.

FIG. 7G depicts a perspective views of embodiments of a device for implantation within the eye, showing a cross-section profile of the device.

FIG. 7H depicts a perspective views of embodiments of a device for implantation within the eye, showing a cross-section profile of the device.

FIG. 8 depicts a perspective views of embodiments of a device for implantation within the eye.

FIG. 9 depicts a schematic top view of embodiments of a device for implantation within the eye.

FIG. 11 depicts embodiments of a capsular tension ring that is configured to limit the outflow of aqueous humor from the eye.

DETAILED DESCRIPTION

This disclosure relates to an eye pressure regulated animal model of reversible elevated eye pressure created in animals (i.e., rabbits, monkeys, etc.) to mimic human glaucoma by blocking the outflow pathway of fluid. Assessment can be made in vivo using ocular imaging technology including, but not limited to, anterior segment imaging (i.e., OCT), and outflow measurements will be made to assess the degree of blockage of flow by techniques such as tonography.

The effect of the elevated eye pressure in vivo on the posterior segment, specific damage to the optic nerve head, and retinal ganglion cells in the retina will also be assessed at the cellular level using, for example, adaptive optics. Multiple applications are available with the model and the associated systems and methods, and these applications will be assessed in vivo, including studying the pathogenesis of glaucoma from normal to end-stage disease, the degree and duration of pressure elevation necessary to cause damage to the optic nerve, assessment of the time duration of possible reversibility of changes in the posterior aspect of the eye by normalizing the eye pressure, and drug studies to evaluate potential candidate molecules, delivery systems, etc., to halt, stabilize or prevent damage to the optic nerve that can lead to the development of glaucoma. Utilizing an eye examining apparatus, such as the slit lamp biomicroscope, applanation tonometry, gonioscopy and fundus photography, will enable clinical assessment with documentation over time.

In some embodiments, a pressure regulating device is utilized, once standardized, to treat human eye conditions, such as hypotony (low eye pressure), if when chronic, can lead to debilitating loss of vision due to very low pressure that otherwise cannot be normalized by other means.

In glaucomas associated with an elevation in eye pressure (intraocular hypertension), the source of resistance to outflow of aqueous humor is mainly in the trabecular meshwork. The tissue of the trabecular meshwork allows the aqueous humor ("aqueous") to enter Schlemm's canal, which then empties into aqueous collector channels in the posterior wall of Schlemm's canal and then into aqueous veins, which form the episcleral venous system. Aqueous humor is a transparent liquid that fills the region between the cornea, at the front of the eye, and the lens.

Figure 1:
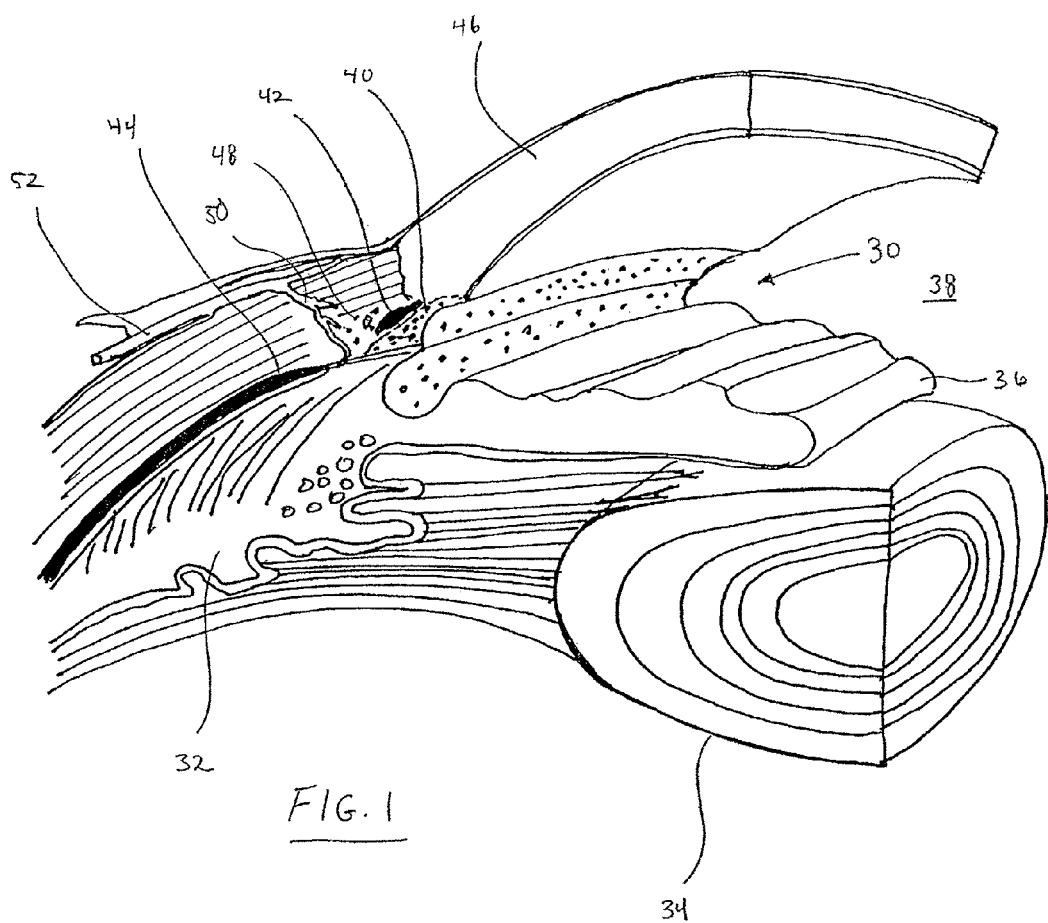
FIG. 1 depicts the anterior chamber and posterior chamber of the anterior segment of an eye, showing the anterior chamber angle of the eye.

With reference to FIG. 1, which depicts the anterior chamber angle 30 of an eye, aqueous humor is continuously secreted by ciliary body 32 which extends around the lens 34 of the eye. The aqueous humor travels from the ciliary body 32 in the posterior chamber of between the lens 34 and the iris 36, and into the anterior chamber 38 of the eye, creating an essentially constant flow of aqueous humor from the ciliary body 32 to the eye's anterior chamber 38. The anterior chamber 38 pressure is determined by a balance between the production of aqueous humor and its exit through the outflow pathways of the eye. The outflow pathways include trabecular meshwork 40, via Schlemm's canal 42 (major route) or uveal scleral outflow, via suprachoroidal space 44 (minor route). The trabecular meshwork 40 is located between an outer rim of the iris 36 and the back of the cornea 46, in the anterior chamber angle 30. The portion of the trabecular meshwork 40 adjacent Schlemm's canal 42 is understood to cause most of the resistance to aqueous outflow in chronic glaucoma. From Schlemm's canal 42, the aqueous humor is conducted via collector channels 48 and aqueous veins and 50 to episcleral veins 52, which drain the aqueous humor from the eye.

Some animal models of glaucoma, such as those induced in monkeys utilizing laser application to the outflow pathway to destroy it in an effort to raise intraocular eye pressure, are not reproducible. These models often require more than one session to raise the eye pressure and are not predictable with respect to either the duration or height of that elevation. Additionally, such destruction of the outflow pathway does not mimic human glaucoma, the most common type being open angle (i.e., open sink) glaucoma, where there is obstruction to outflow due to this regulation at the cellular level as opposed to the laser induced destruction with subsequent physical blockage from scar formation of the outflow pathway.

A number of prototypes of this novel device can enable researchers to deliberately and reproducibly raise the eye pressure by a controlled means of "physically blocking outflow" by titrating the number of degrees of optimal blockage necessary in a total of 360 degrees to achieve the desired elevation. Threshold eye pressure elevation will be determined at which optic nerve head damage ensues enabling the study of early changes at the cellular level using ocular imaging technology. If early pathways of dysfunction are identified with respect to the location, distribution, and extent of retinal ganglion cell death or compromise in the retina or loss of axons (wires) that converge to form the optic nerve head, this will enable targeted drug delivery to where it is needed to avert further damage.

The processes described herein can be assessed in vivo from a healthy eye to early, moderate, and advanced damage. This has not been possible in the history of glaucoma research before. By understanding the sequence of events unfolded in vivo, and knowing the story of, better therapeutic strategies in treating glaucoma can be evaluated by a non-pressure reducing mechanism. Existing treatment algorithms and methods focus primarily on lowering eye pressure, the only FDA approved means of treating patients with glaucoma, either by medical, laser, or surgical means. No other alternative treatment exists today. It has been estimated that over 60 million people worldwide will succumb to glaucoma by 2010, increasing to 80 million by 2020 (British Journal of Ophthalmology, February 2006). Studies such as the one described herein are instrumental in enabling us to get a better handle and understanding glaucoma, a field that has not shown a significant progress other than the lowering of eye pressure over the last half of the century.

In some methods, dimensions of the eye to be treated are acquired, and devices described herein can be selected based the dimensions. In some embodiments, anterior segment OCT imaging is one potential modality for obtaining in vivo measurements. Several dimensions from a plurality of patients can be taken in order to "normalize" data relating to the dimensions. The devices can then be manufactured according to the normalized dimensions or according to the specific dimensions of the patient to be treated. For example, in the context of animal studies, normalized data may be used to manufacture several devices that can be used during the animal studies. In some embodiments, a pre-insertion ocular image can be obtained followed by insertion of the device into the eye, which involves a procedure that is considered minimally invasive and that requires less than one minute, based on procedures for implanting capsular tension rings for cataract surgery, to perform.

In some embodiments, a pressure regulating device is provided that is similar to devices used in observations of eye pressure elevation in rabbits during preclinical testing of capsular tension rings within the lens capsule itself in the posterior segment. The embodiments described herein provide for implantation of such rings in a different location for effecting the physiologic changes sought in this disclosure. Pre- and post-imaging can enable modification to the device if necessary to properly position the implant into the sink to adequately block outflow without compromising the integrity of the eye, such as excessive pressure elevation that can lead to clouding of the cornea or vascular compromise to the eye from the device itself. The clarity of the cornea is desirable for subsequent imaging of the posterior segment to assess the retina and optic nerve.

The number of clock hours or degrees of blockage by the device can be assessed to determine the effect on raising the intraocular pressure. With the established animal model in the rabbit, further support can be used to create a similar model in monkeys, nonhuman primates in whom the glaucomatous process is even more similar to humans. The choice of the rabbit for testing this device can be used because the anterior segment of the rabbit is very similar to that found in humans, and, given the potential application of this device in humans, results of the rabbit and monkey studies can lay the groundwork for improving treatments available to humans.

Figure 2:
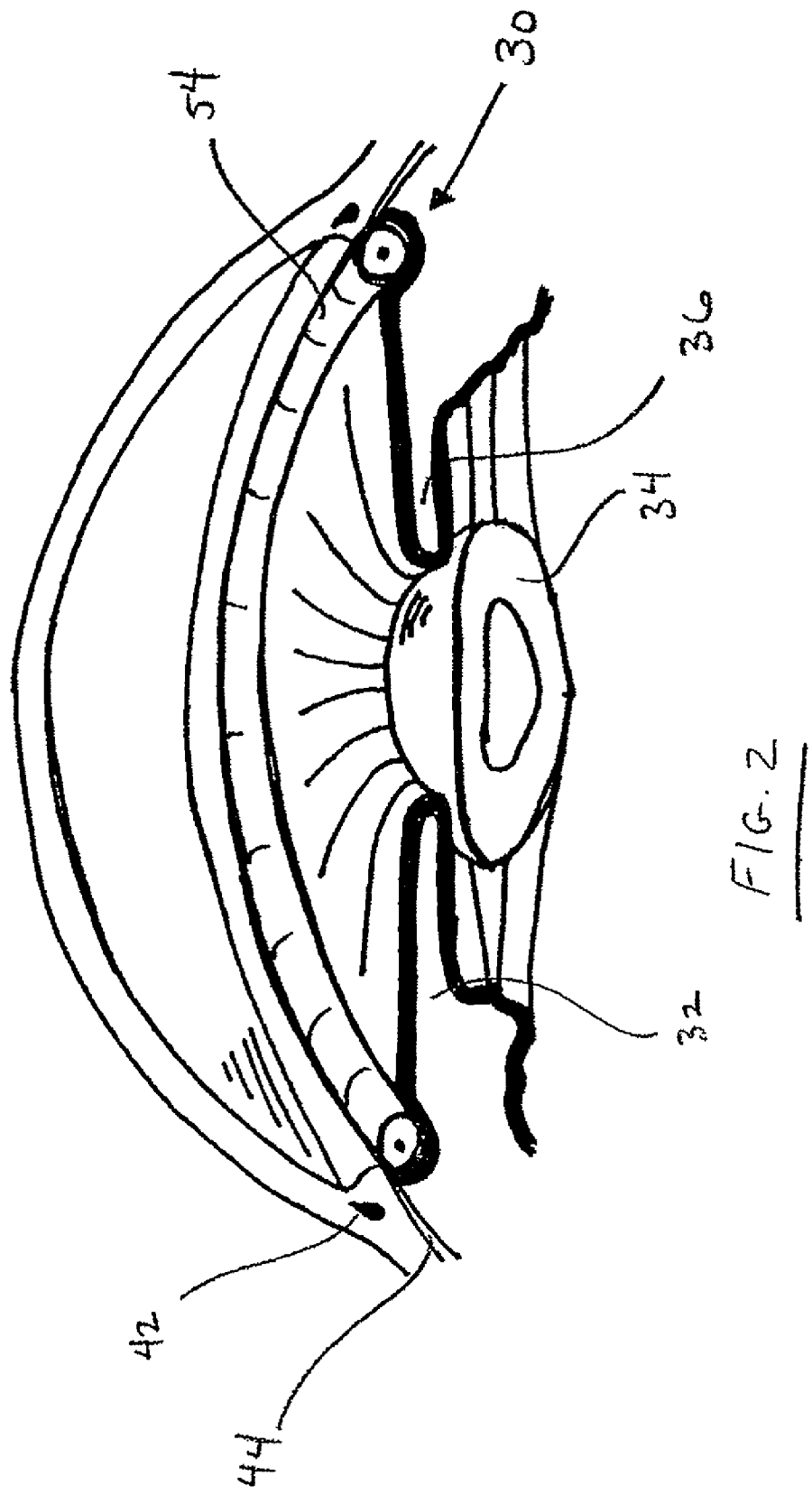
FIG. 2 depicts embodiments described herein for implanting a device in the anterior chamber angle to limit the outflow of aqueous humor from the eye.
Figure 3:
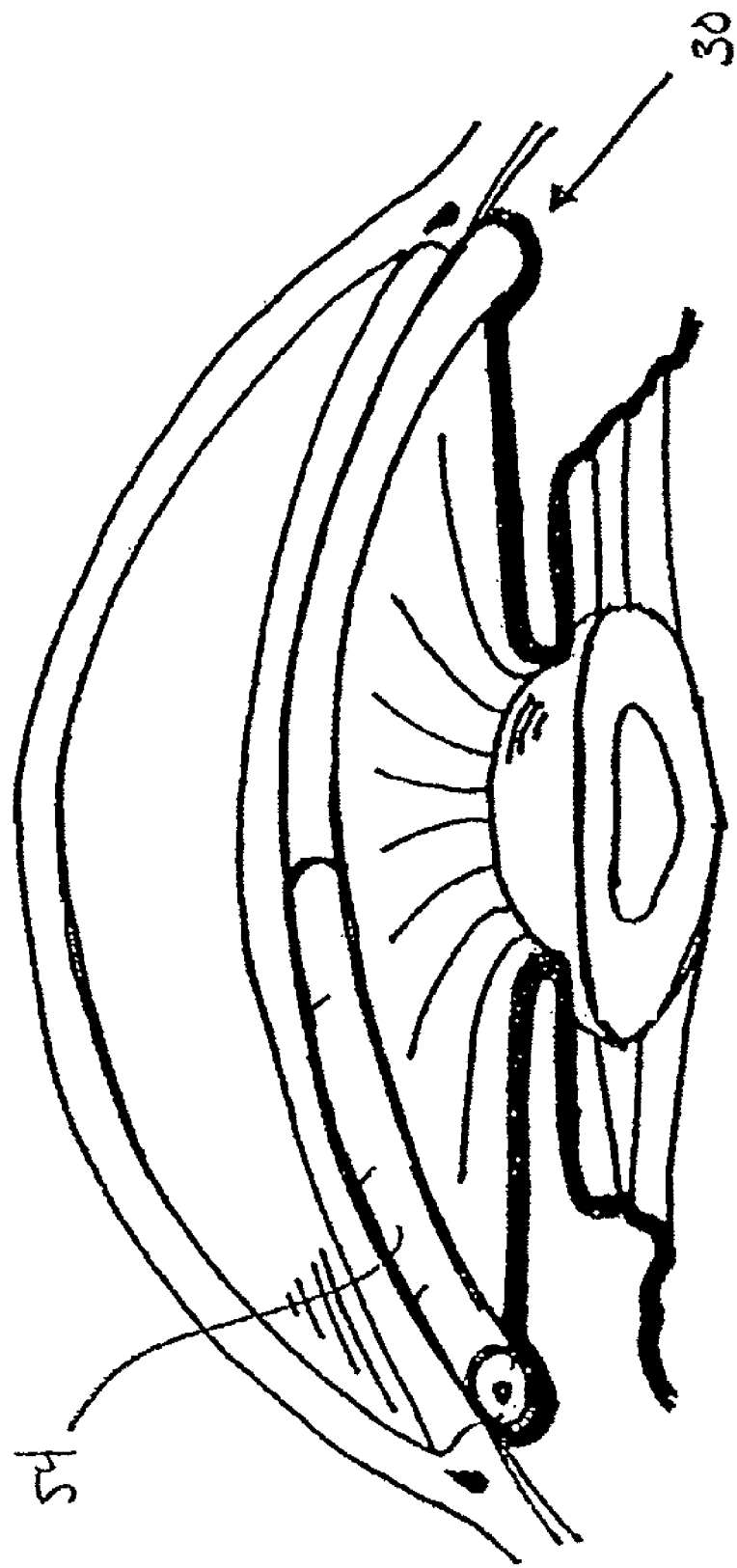
FIG. 3 depicts embodiments described herein for devices that limit the outflow of aqueous humor from the eye.

With reference to FIG. 2, embodiments of a device 54 or illustrated, with the device 54 being implanted within the anterior chamber angle 30 of an eye. As illustrated, the device 54 is positioned at a location in the anterior chamber angle 30 adjacent Schlemm's canal 42 and the suprachoroidal space 44. Accordingly, aqueous humor that is generated by the ciliary body 32 and passes between the iris 36 and the lens 34 is limited in its egress from the eye through the outflow pathways. The device 54 is illustrated as extending at least halfway around the circumference of the anterior chamber angle 30. In some embodiments, the device 54 is configured to abut or block tissue or pathways through which the aqueous humor flows out of the eye. By blocking the tissue or pathways, the fluid is unable to leave the eye and accumulates in greater quantities within the eye. As the fluid accumulates within the eye, the intraocular pressure of the eye increases, simulating conditions consistent with chronic glaucoma. In some embodiments, as illustrated in FIG. 3, the device, 54 can extend only part way around the circumference anterior chamber angle 30.

Figure 4:
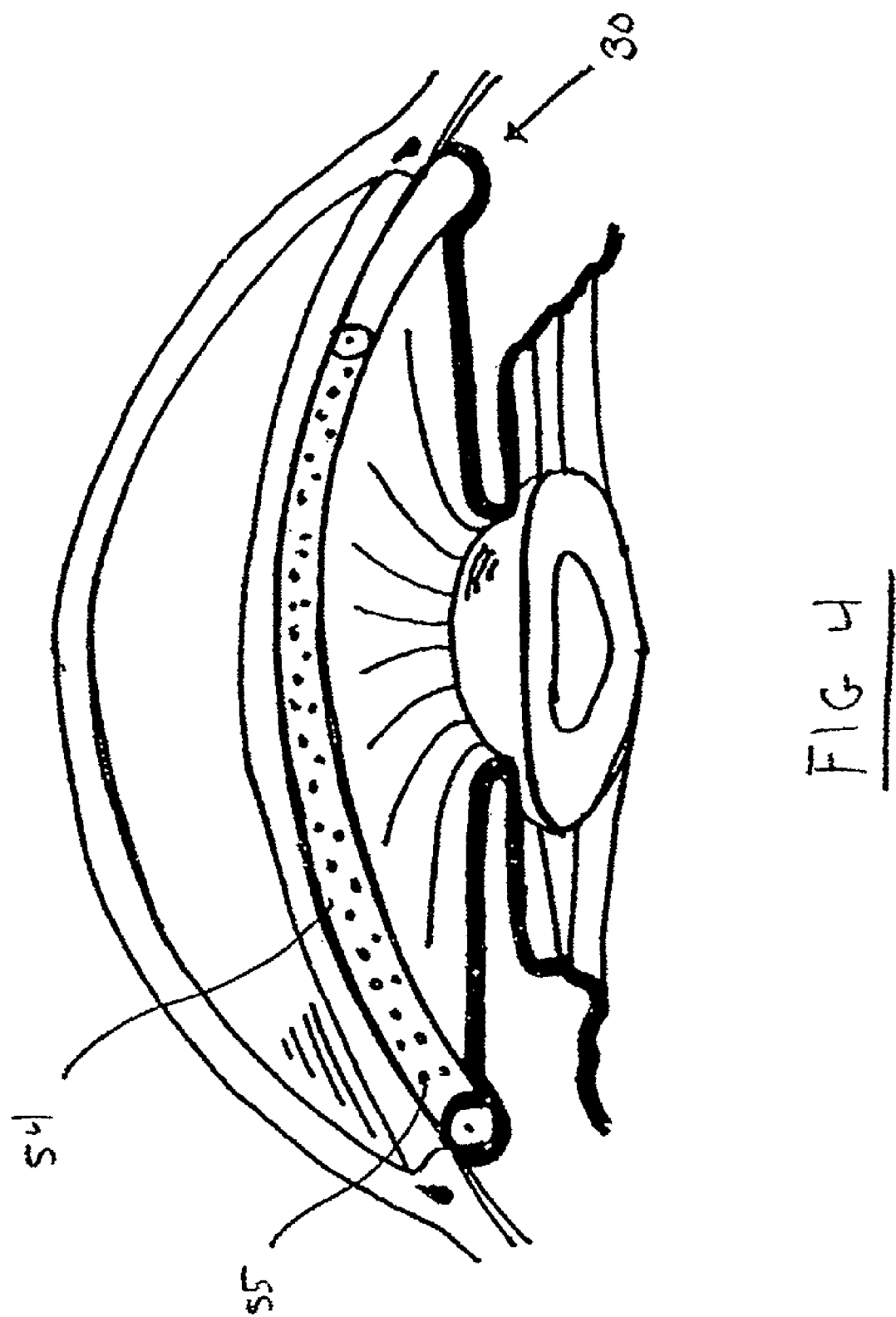
FIG. 4 depicts embodiments described herein for devices that limit the outflow of aqueous humor from the eye.

FIG. 4 depicts embodiments of the device 54 positioned in the anterior chamber angle 30 of the eye. In FIG. 4, the device 54 is depicted as having a porous structure, in contrast to the solid structure depicted in FIGS. 2 and 3. The porous structure can be used to allow a limited or predetermined amount of aqueous flow past the device. Accordingly, some embodiments described herein disclose a means for preventing aqueous flow past a device positioned in the eye, and other embodiments described herein disclose a means for limiting or regulating the aqueous flow past a device positioned in the anterior chamber angle 30 of an eye. In some embodiments, the device 54 can include apertures 55 positioned axially along the device 54, which allow flow of aqueous humor therethrough to the outflow pathways.

Figure 5:
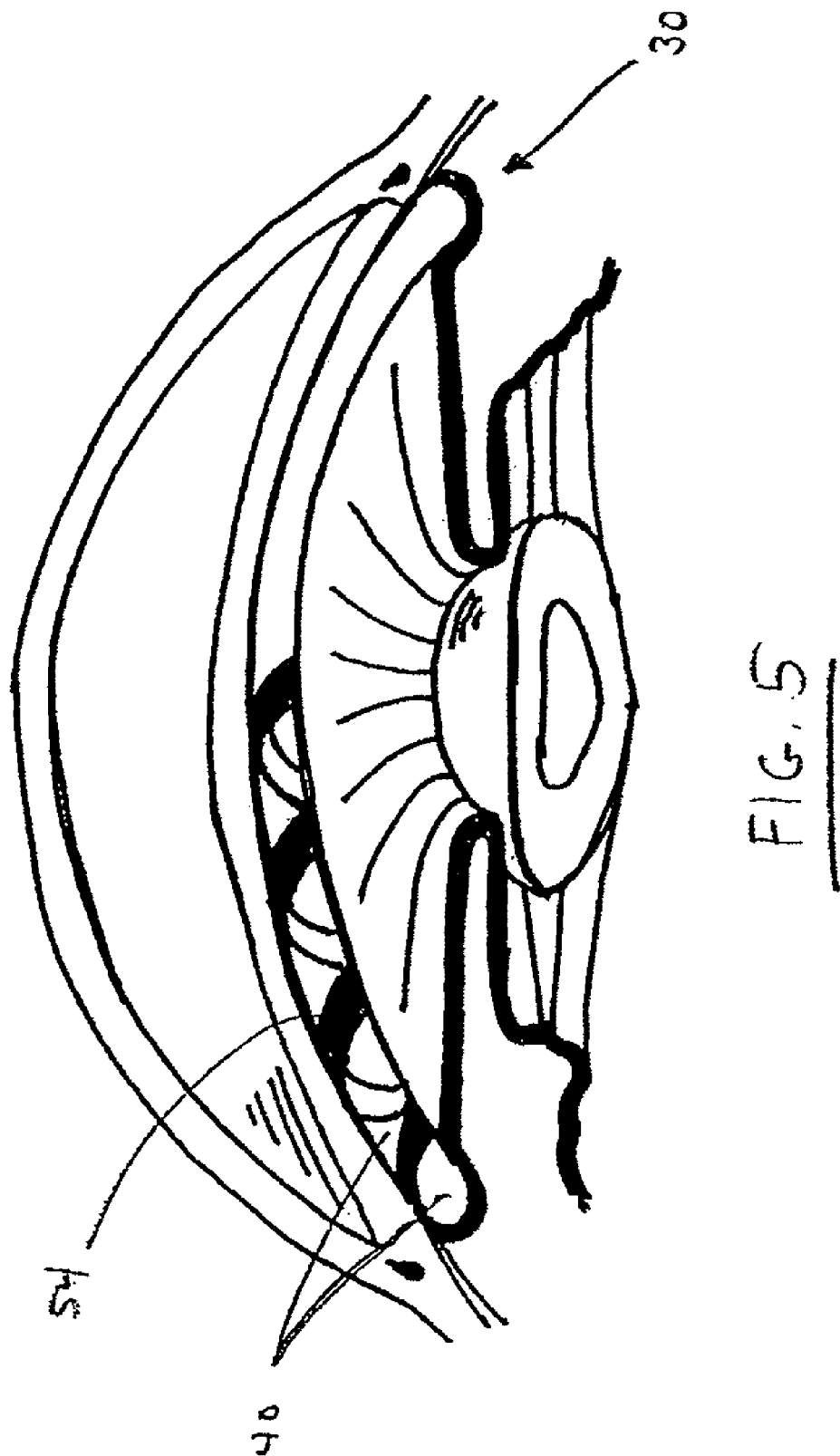
FIG. 5 depicts embodiments described herein for devices that limit the outflow of aqueous humor from the eye.

FIG. 5 illustrates embodiments of the device 54 positioned in the anterior chamber angle 30 of the eye, in which the device 54 has a spiral or coil-like structure. In these embodiments, the device 54 can operate to limit or reduce the flow of aqueous humor through portions of the trabecular meshwork 40. A pitch of the spiral or coil like structured device 54 can be varied depending upon the surface area of the trabecular meshwork 40 that is desired to be blocked.

FIGS. 6A-6G illustrate examples of different lengths of the device 54. FIG. 6A depicts an embodiment of the device 54 in which the device 54 is configured to extend the full circumference of the anterior chamber angle 30. Accordingly, the device extends 360° around the anterior chamber angle 30 of the eye. FIG. 6B depicts an embodiment of the device 54 in which the device extends about 315° around the anterior chamber angle 30 of the eye. FIG. 6C depicts an embodiment of the device 54 in which the device extends about 270° around the anterior chamber angle 30 of the eye. FIG. 6D, depicts an embodiment of the device 54 in which the device extends about 225° around the anterior chamber angle 30 of the eye. FIG. 6E depicts an embodiment of the device 54 in which the device extends about 180° around the anterior chamber angle 30 of the eye. FIG. 6F depicts an embodiment of the device 54 in which the device extends about 135° around the anterior chamber angle 30 of the eye. FIG. 6G depicts an embodiment of the device 54 in which the device 54 extends about 90° around the anterior chamber angle 30 of the eye. Accordingly, in some embodiments, the device 54 can extend from about 90° to about 360° around the anterior chamber angle 30 of the eye. In some embodiments, the device 54 can extend less than about 90° around the anterior chamber angle 30 of the eye, and in some embodiments, the device 54 can extend greater than about 360° around the anterior chamber angle 30 of the eye.

In some embodiments, the device 54 includes an arcuate body that extends in an arc of between about 20° and about 360°. In some embodiments, the body extends in an arc of less than about 20° or greater than about 360° (e.g., if the device 54 wraps around, or overlaps, itself). In some embodiments, the body extends in an arc of at least 20°. In some embodiments, the body extends in an arc of at least 40°. In some embodiments, the body extends in an arc of at least 60°. In some embodiments, the body extends in an arc of at least 90°. In some embodiments, the body extends in an arc of at least 120°. In some embodiments, the body extends in an arc of at least 180°. In some embodiments, the body extends in an arc of at least 270°. In some embodiments, the body extends in an arc of at least 360°.

In some applications, the anterior chamber angle 30 has a diameter of from about 10 mm to about 15 mm. In such applications, the device 54 can likewise has a diameter ranging from about 10 mm to about 15 mm. In further embodiments, the device 54 can have a diameter that is less than about 10 mm or greater than about 15 mm. In some embodiments, a largest cross-sectional dimension of the device 54, which can be a diameter of the device 54 in cylindrically shaped devices 54, can range between about 0.5 mm and about 4 mm. In some embodiments, the largest cross-sectional dimension of the device and 54 can be less than about 0.5 mm or greater than about 4 mm.

FIGS. 7A-7H depict examples of different cross-sectional profiles of the device 54. FIG. 7A depicts an embodiment of the device 54 in which the device 54 has a substantially solid circular cross-sectional profile. FIG. 7B depicts an embodiment of the device 54 in which the device 54 has an annular cross-sectional profile, and in which the device 54 has a small, axially extending lumen. FIG. 7C depicts an embodiment of the device 54 in which the device 54 has an annular cross-sectional profile, and in which the device 54 has a large, axially extending lumen. FIG. 7D depicts an embodiment of the device 54 in which the device 54 has a substantially semi-circular cross-sectional profile. FIG. 7E depicts an embodiment of the device 54 in which the device 54 has a substantially semi-annular cross-sectional profile. FIG. 7F depicts an embodiment of the device 54 in which the device 54 has a cross-sectional profile with a concave inner side and a convex outer side. FIG. 7G depicts an embodiment of the device 54 in which the device 54 has a substantially rectangular cross-sectional profile. FIG. 7G depicts an embodiment of the device 54 in which the device 54 has an irregular cross-sectional profile.

FIG. 8 depicts an embodiment of the device 54 in which two adjoining ends of the device 54 have mating portions. For example, in some embodiments, a proximal end 58 of the device 54 can include a recessed portion 60. A distal end 62 of the device 54 can include a protruding portion 64. In some embodiments, the recessed portion 60 is configured to receive the protruding portion 64, such that as the protruding portion 64 extends into the recessed portion 60, the proximal end 58 and the distal end 62 of the device 54 are conjoined.

In some embodiments, as depicted by the device 54 illustrated in FIG. 9, the device 54 can include shape memory or biasing materials. In some embodiments, the device 54 is configured to expand outward, as depicted by the arrows 66.

Figure 10:
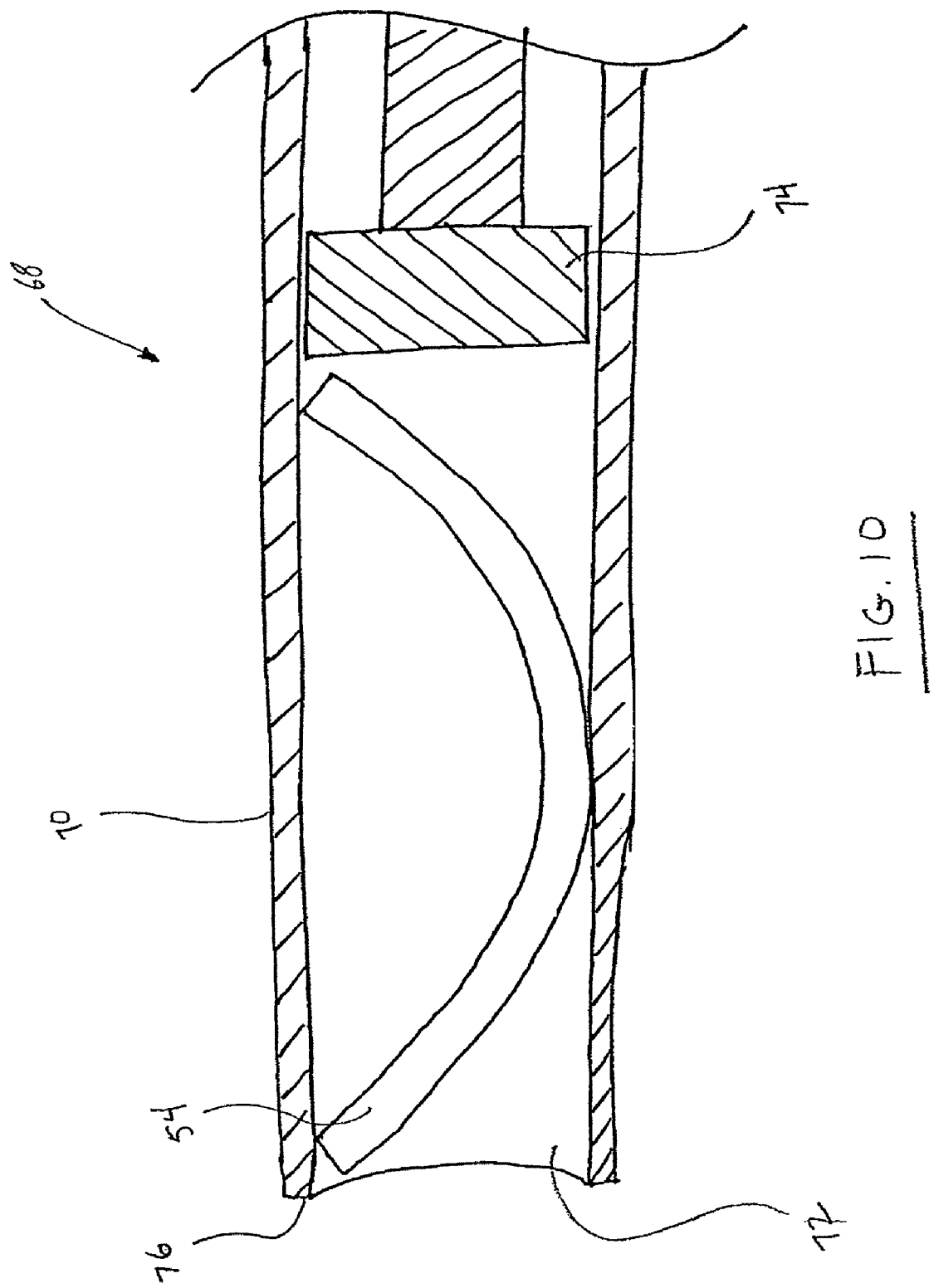
FIG. 10 depicts embodiments for a delivery device for implanting a device within the eye.

FIG. 10 illustrates embodiments of a delivery system 68 that is configured to deliver the device 54 to the eye. In some embodiments, the delivery system 68 includes a distal portion 70 having a lumen 72 extending therethrough. In some embodiments, the device 54 is positioned within the lumen 72 of the distal portion 70 prior to deployment of the device 54 inside the eye. A pusher 74 can extend within the lumen 72 of the distal portion 70 proximate to the device 54. The pusher 74 is preferably axially movable within the lumen 72 so as to be able to move distantly along the lumen and move the device 54 toward and out of a distal end 76 of the delivery system 60.

FIG. 11 depicts embodiments in which a haptic intraocular lens 78 is positioned within a capsular bag 80 of the eye. In some embodiments, the intraocular lens 78 is configured to distend the capsular bag 80, such that the flow of aqueous humor is impeded, and results in an increased intraocular pressure.

The device 54 described herein may be manufactured or fabricated by a wide variety of techniques. These include, without limitation, molding, thermo-forming, or other micromachining techniques, among other suitable techniques.

The device 54 preferably comprises a biocompatible material such that inflammation arising due to irritation between the outer surface of the device 54 and the surrounding tissue is minimized. Biocompatible materials which may be used for the device 54 preferably include, but are not limited to, titanium, titanium alloys, medical grade silicone, e.g., SILASTIC™, available from Dow Corning Corporation of Midland, Mich.; and polyurethane, e.g., PELLETHANE™, also available from Dow Corning Corporation.

In some embodiments, the device 54 may include other types of biocompatible material, such as, by way of example, polyvinyl alcohol, polyvinyl pyrolidone, collagen, heparinized collagen, polytetrafluoroethylene, expanded polytetrafluoroethylene, poly(methyl methacrylate) (PMMA), fluorinated polymer, fluorinated elastomer, flexible fused silica, polyolefin, polyester, polysilicon, and/or a mixture of the aforementioned biocompatible materials, and the like. In some embodiments, composite biocompatible material may be used, wherein a surface material may be used in addition to one or more of the aforementioned materials. For example, such a surface material may include polytetrafluoroethylene (PTFE) (such as TEFLON™), polyimide, hydrogel, heparin, therapeutic drugs (such as beta-adrenergic antagonists and other anti-glaucoma drugs, or antibiotics), and the like.

In some embodiments of the surgery, the patient is placed in the supine position, prepped, draped and anesthetized. A small (e.g., less than about 1 mm) incision, which may be self sealing can then be made through the cornea 46. The corneal incision can be made in a number of ways, for example, by using a micro-knife, among other tools. Similar procedures for creating an opening in the eye can also be used. For example, the opening may be created by the procedures of an ocular paracentesis.

The delivery system 68 is used to advance the device 54 through the corneal incision and to the anterior chamber angle 30. With the device 54 held by the delivery system 54, pusher 74 is advanced through the lumen 72 of the delivery system

68. The device 54 is advanced until it is ejected from the distal end 76 of the system 68. Advantageously, in some embodiments, the distal end 76 of the delivery system 68 can include a self-trephining edge that allows for a "single-step" procedure to make the corneal incision and to deliver the device 54 in the proper orientation and alignment within the eye to the anterior chamber angle 30. Desirably, this provides for a faster, safer, and less expensive surgical procedure.

Although preferred embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above.

What is claimed is:

1. A method, of elevating intraocular pressure in a mammalian eye, comprising:

inserting a device, comprising an arcuate body, along an arc of at least 90 degrees in the iridocorneal angle of the eye and in contact with the trabecular meshwork such that a placement of the device along the arc impedes outflow of aqueous humor through the trabecular meshwork, thereby increasing intraocular pressure within the eye.

2. The method of claim 1, further comprising adjusting an amount of obstruction of the outflow.

3. The method of claim 1, further comprising selecting a size of the device, prior to the inserting, using ocular imaging.

4. The method of claim 1, further comprising modeling glaucoma using the device after the inserting of the device in the eye.

5. The method of claim 1, further comprising treating hypotony of the eye using the device by the inserting of the device in the eye.

6. The method of claim 1, wherein the device comprises at least one aperture, and the device is inserted such that aqueous humor passes through the at least one aperture in the device.

7. The method of claim 1, wherein the device comprises pores, and the device is inserted such that aqueous humor passes through the pores in the device.

8. The method of claim 1, further comprising inducing ischemia in the trabecular meshwork.

9. The method of claim 1, wherein the device is inserted along an arc of at least 180 degrees in the iridocorneal angle of the eye.

10. The method of claim 1, wherein the device is inserted along an arc of at least 270 degrees in the iridocorneal angle of the eye.

* * * * *